United States Patent
May et al.

(10) Patent No.: US 8,522,614 B2
(45) Date of Patent: Sep. 3, 2013

(54) IN-LINE INSPECTION METHODS AND CLOSED LOOP PROCESSES FOR THE MANUFACTURE OF PREPREGS AND/OR LAMINATES COMPRISING THE SAME

(75) Inventors: Andrzej Michael May, Schenectady, NY (US); Waseem Ibrahim Faidi, Schenectady, NY (US); Shu Ching Quek, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 350 days.

(21) Appl. No.: 12/787,464

(22) Filed: May 26, 2010

(65) Prior Publication Data
US 2011/0135872 A1 Jun. 9, 2011

(51) Int. Cl.
*G01H 9/00* (2006.01)

(52) U.S. Cl.
USPC .................. 73/570; 73/583; 73/866.5

(58) Field of Classification Search
USPC ............... 73/570, 583, 597, 866.5; 428/98; 156/157; 264/407
See application file for complete search history.

(56) References Cited

U.S. PATENT DOCUMENTS

| | | | | |
|---|---|---|---|---|
| 3,960,650 A * | 6/1976 | Parks et al. | ............. | 162/103 |
| 5,181,421 A * | 1/1993 | Kline | ............. | 73/597 |
| 5,266,139 A * | 11/1993 | Yokota et al. | ............. | 156/169 |
| 6,066,284 A * | 5/2000 | Hunt et al. | ............. | 264/407 |
| 6,359,107 B1 | 3/2002 | Connell et al. | | |
| 6,696,692 B1 | 2/2004 | Pepper | | |
| 6,843,565 B2 | 1/2005 | Evans et al. | | |
| 7,056,585 B2 * | 6/2006 | Mishima et al. | ............. | 428/413 |
| 7,166,251 B2 | 1/2007 | Blankinship | | |
| 7,536,271 B2 | 5/2009 | Marsh et al. | | |
| 7,650,790 B2 | 1/2010 | Wright | | |
| 8,048,815 B2 * | 11/2011 | Kubota et al. | ............. | 442/286 |
| 2004/0094851 A1 | 5/2004 | Mbachu et al. | | |
| 2008/0134749 A1 | 6/2008 | Engelbart et al. | | |
| 2008/0229834 A1 | 9/2008 | Bossi et al. | | |
| 2008/0315462 A1 * | 12/2008 | Batzinger et al. | ............. | 264/407 |
| 2009/0146433 A1 * | 6/2009 | Althoff et al. | ............. | 290/55 |
| 2009/0284752 A1 | 11/2009 | Lorraine et al. | | |
| 2011/0114252 A1 * | 5/2011 | Partington et al. | ............. | 156/157 |

FOREIGN PATENT DOCUMENTS

| | | |
|---|---|---|
| EP | 1046666 A1 | 10/2000 |
| JP | 2007265863 A | 10/2007 |
| WO | 2009063398 A2 | 5/2008 |
| WO | 2008070705 A2 | 6/2008 |

OTHER PUBLICATIONS

Advanced for the Topographic Characterization of SMC materials, Calvimontes et al., 2009.*
Search Report from corresponding EP Application No. 11166987.5-2204 dated Sep. 21, 2011.

* cited by examiner

*Primary Examiner* — J M Saint Surin
(74) *Attorney, Agent, or Firm* — Ann M. Agosti (57) ABSTRACT

In-line inspection methods are provided. The methods comprise measuring at least two parameters/properties of a prepreg and/or laminate during the manufacture thereof. In some embodiments, the data collected using the inline inspection methods may be processed and/or provided to a manual or automated controller, in order to provide a closed loop method for the manufacture of the prepregs and/or laminates. Apparatus for carrying out the methods are also provided, as are articles comprising a prepreg and/or laminate made using the apparatus.

7 Claims, 4 Drawing Sheets

IN-LINE INSPECTION METHODS AND CLOSED LOOP PROCESSES FOR THE MANUFACTURE OF PREPREGS AND/OR LAMINATES COMPRISING THE SAME

FIELD

The embodiments disclosed relate generally to in-line inspection methods and closed loop methods for the manufacture of prepregs and/or laminates incorporating these.

BACKGROUND

Composite materials have been used to produce both lightly loaded and highly loaded structures, useful in non-load carrying and load carrying applications, respectively. Examples of the former include boat hulls and automobile body panels, while examples of the latter include pressure vessels, frames, fittings and aircraft fuselages. Because of their wide applicability, composite materials have found use in the automotive, marine and aerospace industries. However, due to their ability to be manufactured in forms suitable for bearing heavy loads, composite materials are particularly ubiquitous in the design of load bearing structural members.

Composite materials typically include a fibrous material, such as carbon, aramid, glass or quartz, bonded together with a resin material, such as an epoxy. The load in such composite materials is carried primarily by the fibrous material, and so, the load carrying properties of the composite can be altered by altering the orientation of the fibers in the composite material. For example, composite materials with unidirectional fibers, such as tapes or tows, may generally exhibit the strongest tensile strength along the axis of the fibers. Woven fabrics and bi-directional mats are typically strongest in the plane of the material. Thus, when designing composite materials, fiber orientation and the number of layers, also known as plies, is typically specified in consideration of the anticipated load the composite item will experience.

Fiber composite laminates or parts may typically be manufactured by first impregnating the fiber reinforcement with resin to form a prepreg, and then consolidating two or more layers of prepreg into a laminate. Inherent in the layup process used to form such materials are the formation of a variety of defects, including wrinkles, voids, delaminations, and the like. For example, voids in the prepreg and/or laminate, may result from the inefficient penetration of the resin in to the fiber bundle, tow, or roving, or from outgassing during the consolidation process. Such defects may be formed in greater number when the composite article being formed is relatively large, or incorporates a contour, or otherwise complex shape.

Many times, such defects may not be on the surface or otherwise be immediately detectable during the layup process, or, such defects may become visible or exacerbated during the curing process. The presence of such defects in the finished article can de-rate the material strength up to a factor of 2, and so, may require that the article be repaired, or, may even require that the part be scrapped, thus contributing to an increase in manufacturing cost due to either the repair cost and/or lead-time required to replace scrapped articles.

Many inspection methods have been applied independently to composite materials. However, the resolution of defects when using some of these composite materials may limited in some applications. For example, in composite materials wherein the fibers or tows have a random orientation, or in composite materials wherein the fibers desirably comprise carbon, either the structure or the carbon may scatter the measured signal. Further, in many applications, it may be desirable, or even necessary, to obtain multiple measurements, including both measurements of physical parameters and material properties, of the composite material. Many inspection apparatus' are capable of providing only one measurement, or type of measurement, or provide data with a standard deviation unacceptable in some applications. And, equipment capable of conducting more sophisticated measurements can be expensive and thus not cost-effective in applications where the profit margin of the article being manufactured does not warrant the expense.

It would therefore be desirable to develop new inspection methods capable of being incorporated inline. Such methods would desirably allow defects to be detected and compensated for during the manufacture of composite materials, and as a result, reduce or eliminate the amount of rework or scrap that can be produced by conventional manufacturing processes.

BRIEF DESCRIPTION

There is provided an in-line inspection method comprising measuring at least two parameters and/or properties of a prepreg and/or laminate during the manufacture thereof.

In another aspect, there is provided a method for the manufacture of a prepreg and/or laminate comprising conducting at least one step of a prepreg and/or laminate manufacturing process and measuring at least two properties of the prepreg and/or laminate before, during or after the at least one step.

In another aspect, there is provided an apparatus for the manufacture of a prepreg and/or laminate. The apparatus comprises a controller, a resin infusion apparatus, at least one measurement apparatus, and a processor. The processor is operatively disposed relative to the measurement apparatus and controller so that information may be transmitted therebetween. Articles prepared from prepregs and/or laminates made using the apparatus are also provided.

BRIEF DESCRIPTION OF THE DRAWINGS

These and other features, aspects, and advantages of the present invention will become even better understood when the following detailed description is read with reference to the accompanying drawings in which like characters represent like parts throughout the drawings, wherein.

DETAILED DESCRIPTION

The above brief description sets forth features of the various embodiments of the present invention in order that the detailed description that follows may be better understood, and in order that the present contributions to the art may be better appreciated. There are, of course, other features of the invention that will be described hereinafter and which will be for the subject matter of the appended claims.

In this respect, before explaining several embodiments of the invention in detail, it is understood that the various embodiments of the invention are not limited in their application to the details of the construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The terms "first," "second," and the like, as used herein do not denote any order, quantity, or importance, but rather are used to distinguish one element from another. The terms "a" and "an" herein do not denote a limitation of quantity, but rather denote the presence of at least one of the referenced items. The modifier "about" used in connection with a quantity is inclusive of the stated value, and has the meaning dictated by context, (e.g., includes the degree of error associated with measurement of the particular quantity). The suffix "(s)" as used herein is intended to include both the singular and the plural of the term that it modifies, thereby including one or more of that term.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Embodiments of the subject matter disclosed relate generally to in-line inspection methods. The methods comprise measuring at least two parameters/properties of a prepreg and/or laminate during the manufacture thereof. In some embodiments, the data collected in the inline inspection methods may be processed and/or provided to a manual or automated controller, in order to provide a closed loop method for the manufacture of the prepregs and/or laminates. Apparatus for carrying out the methods are also provided, as are articles comprising a prepreg and/or laminate made using the apparatus.

Figure 1:
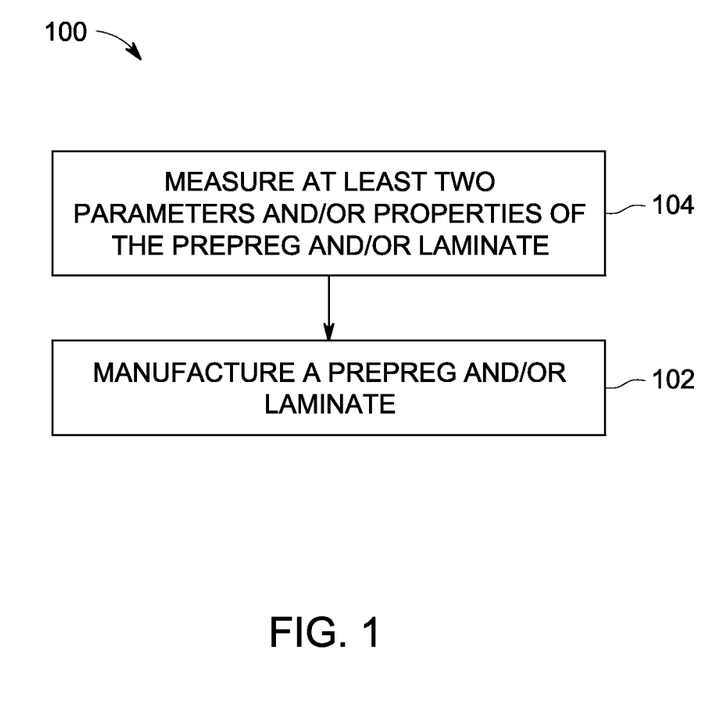
FIG. 1 is a flow chart representing steps in an exemplary inline inspection method in accordance with some embodiments.

FIG. 1 is a flow chart illustrating one embodiment of the method. As shown, method 100 involves manufacturing a prepreg and/or laminate at step 102, and measuring at least two properties of the prepreg and/or laminate during the manufacture thereof at step 104. The measurements may generally be taken at any point in the manufacturing process of a prepreg or laminate, such steps being generally known to those of ordinary skill in the art, and including, resin infusion, compression/compaction, lamination/layup, consolidation and curing.

The properties and/or parameters measured can be any that provide useful information about the prepreg and/or laminate. In some embodiments, the measured properties and/or parameters provide information related to the properties of the prepreg and/or laminate, while in others, the measured properties and/or parameters provide information related to defects, e.g., voids, cracks, foreign inclusions, delaminations, porosity, wrinkles, or fiber misalignment within the prepreg and/or laminate. Desirably, at least two measurements are made so that more information is obtained as compared to methods of inline inspection of prepregs and/or laminates that utilize only one measurement.

In some embodiments, the at least two measurements may be the same measurement, made at different stages of the manufacturing process, while in others, the measurements may be different, and made at the same, or different, stages of the manufacturing process. In certain embodiments, one measurement may comprise one made substantially at, or in relation to, the surface of the prepreg and/or laminate, while the other measurement may be made below the surface, i.e., in relation to the subsurface of the prepreg and/or laminate.

The particular method of measurement(s) will depend upon the property(ies) desirably being measured. Measurement methods for such properties are generally known, and include imaging techniques, such as acoustic holography, optical metrology and many varieties of cameras, e.g., microwave cameras, for dimensional measurements, such as length, width, depth, or measurements made in more than one dimension; thermometers or thermocouples for the measurement of thermal conductivity; magnetometers such as hall-effect sensors, giant magneto-resistive sensors, anisotropic magneto-resistive sensors, atomic magnetometers, superconducting quantum interference devices (SQUIDS) or eddy current coils for the measurement of magnetic permeability; capacitive plates or striplines for the measurement of dielectric constant; ohmmeters and eddy current coils for the measurement of electric conductivity; densitometers, ultrasound or x-ray for the measurement of density or porosity; and magnetometers and coils for the measurement of nuclear quadruple resonance frequency.

In some embodiments, at least one of the measurements provides dimensional information, such as length, width, depth, or measurements made in more than one dimension. Many imaging techniques are available capable of providing such measurements, either directly, or indirectly via an image that may be further analyzed to provide the desired dimensional information. Examples of such imaging techniques include acoustic holography, eddy current array imaging, optical metrology and many varieties of cameras, e.g., microwave cameras.

Figure 2:
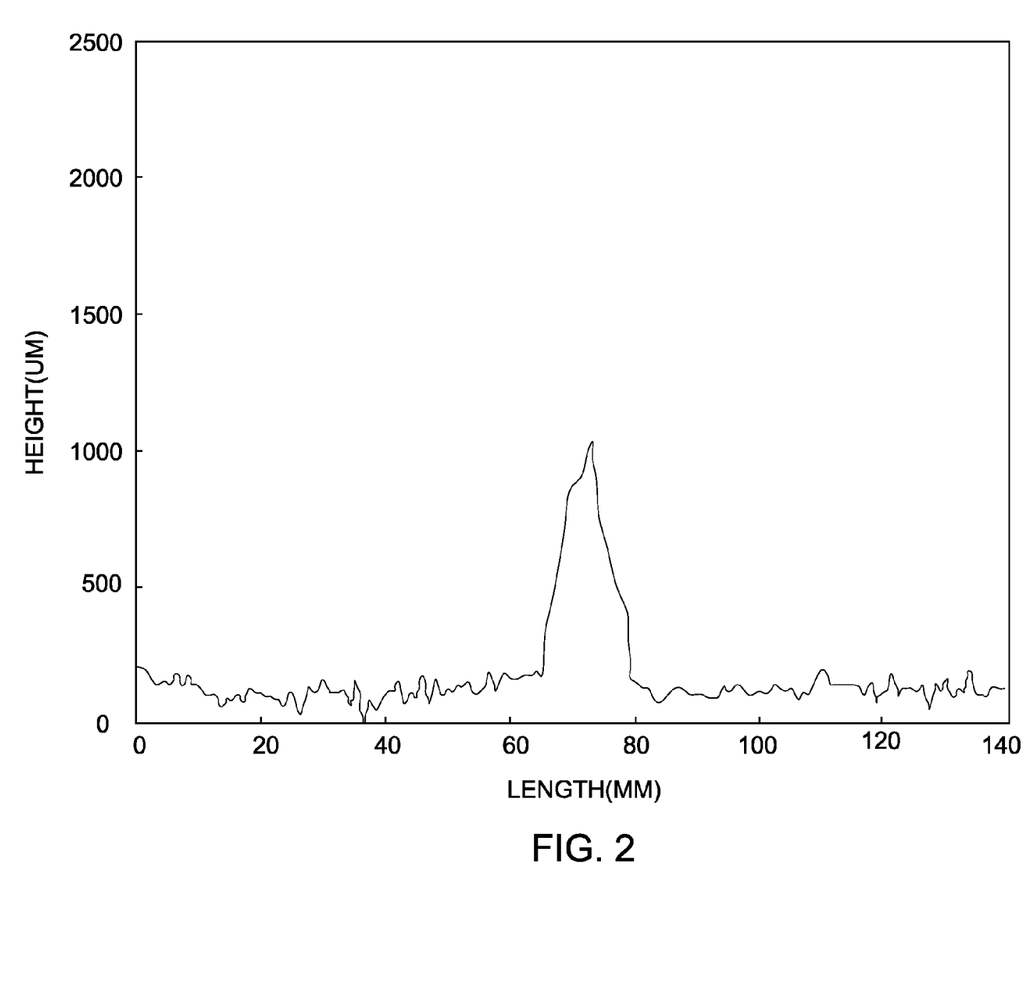
FIG. 2 is a graphical depiction of optical metrology data obtained from a prepreg according to one embodiment.

In some embodiments, optical metrology may be used, and is advantageously capable of providing information related to wrinkles or waviness present in the reinforcement material, prepreg and/or laminate. Optical metrology data obtained from a prepreg according to and/or prepared according to one embodiment is shown in FIG. 2, wherein the peak indicates a wrinkle in the prepreg.

Techniques for conducting optical metrology measurements, as well as analyzing the results thereof, are well known to those of ordinary skill in the art, and are described generally in Yoshizawa, Taoru, *Handbook of optical metrology principals and applications*, Taylor & Francis, Boca Raton, co. 2008 hereby incorporated by reference herein in its entirety. Further, equipment for conducting such measurements is commercially available from a variety of sources including General Electric Company, FARO and Minolta.

Figure 3:
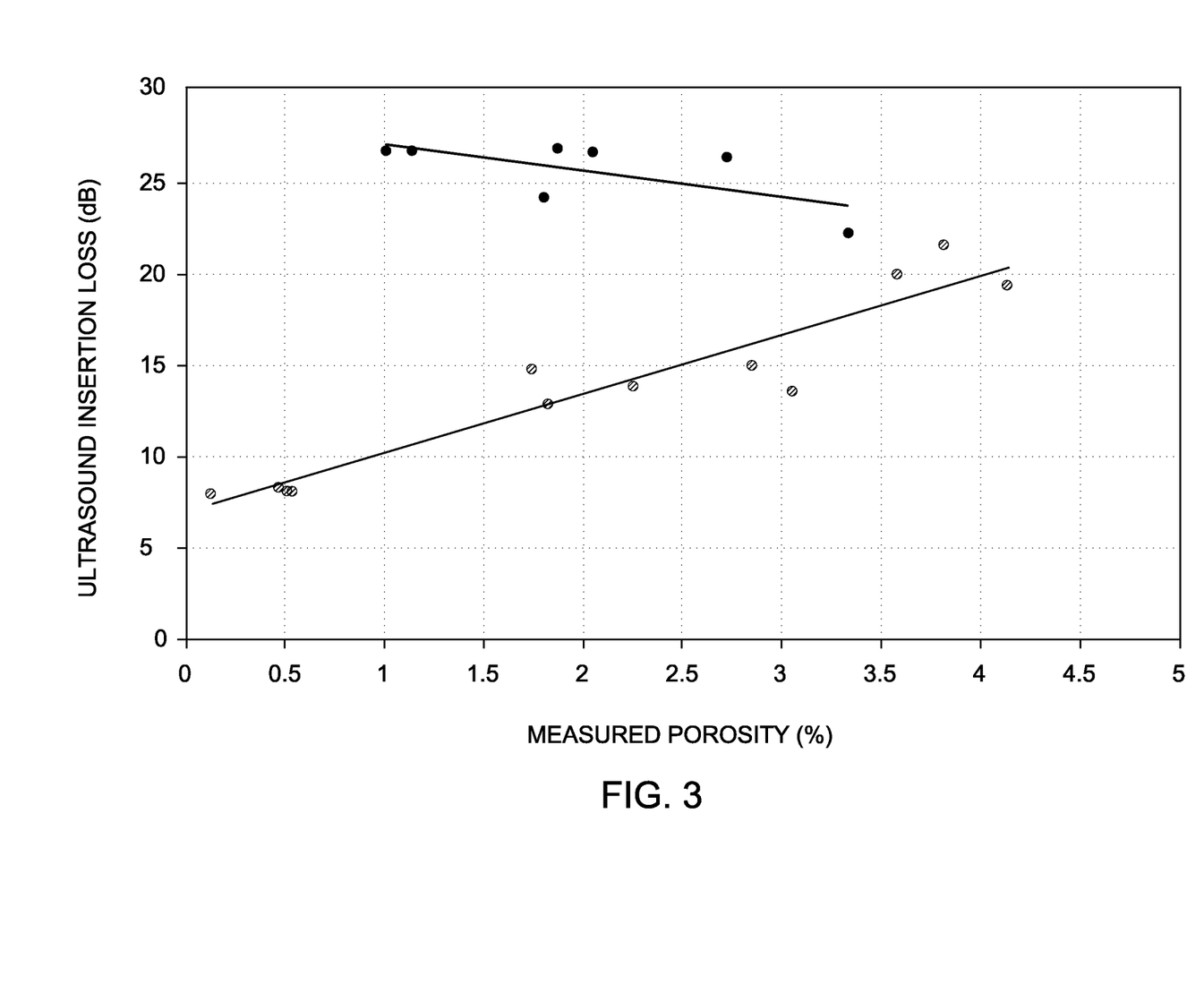
FIG. 3 is a graphical depiction of ultrasound data obtained from a prepreg according to one embodiment.

In some embodiments, at least one of the measurements provides information related to a property of the prepreg or laminate, or the presence of a defect in the same. For example, at least one measurement may desirably provide information related to the thermal conductivity, magnetic permeability, dielectric constant, electric conductivity, density, nuclear quadruple resonance frequency, etc., of the prepreg and/or laminate. In some embodiments, ultrasound measurements are employed and provide information related to the porosity, fiber volume fraction, voids and/or delaminations of the prepreg and/or laminate. Ultrasound data obtained from a prepreg according to and/or prepared according to one embodiment is shown in FIG. 3.

Techniques for conducting ultrasound measurements, as well as analyzing the results thereof, are well known to those of ordinary skill in the art, and are described generally in Data, S. K. and Shah, A. H., *Elastic waves in composite media and structures with applications to ultrasonic nondestructive*

*evaluation*, CRC Press, Boca Raton, co. 2009, hereby incorporated by reference herein in its entirety. Further, equipment for conducting such measurements is commercially available from a variety of sources including General Electric, Olympus, and NDT Systems.

Whatever the measurement method(s) utilized, appropriate sensors, or arrays of sensors, therefore are desirably operatively disposed relative to the prepreg and or laminate, or processing equipment therefore at the point of the manufacturing process at which the measurement information is desirably obtained. In some embodiments, the sensor or array(s) of sensors may advantageously be placed proximal to, distal to, or in close proximity to where the resin is desirably infused into the reinforcement material, and/or compaction/compression of the prepreg, layup of one or more prepregs to provide the laminate, or consolidation of the laminate takes place. Stated another way, at least one of the measurements is taken before, during or after infusion of a resin onto a reinforcement material, a compaction step, a lamination/layup step, a consolidation step and/or a curing step.

In those embodiments wherein optical metrology is employed to obtain one of the measurements, it may advantageously be employed during layup, when it is expected to provide information related to the laminate surface topography. In those embodiments wherein ultrasound measurements are employed, they may advantageously be taken during infusion, and/or prior to, or during compaction, when they are expected to provide information related to the porosity of the prepreg.

In some embodiments, the data obtained from at least one measurement is advantageously used to monitor and/or modify the manufacturing process. In other words, the data obtained from the measurements may, in some embodiments, be provided to a processor capable of manipulating the data. For example, the data may be manipulated to provide a historical overview of the measured property of the prepreg and/or laminate, or, the data may be manipulated in order to predict how the properties and/or defects within prepreg and/or laminate may develop during further processing and/or storage.

Figure 4:
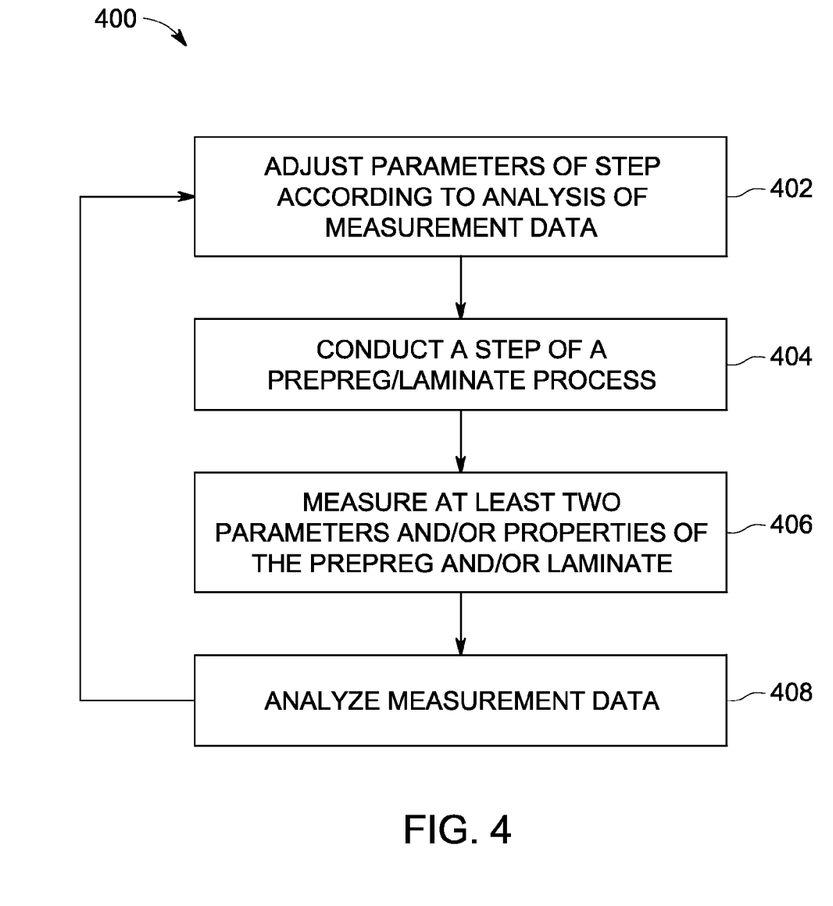
FIG. 4 is a flow chart representing steps in an exemplary inline inspection method in accordance with some embodiments.

Such an embodiment is shown in FIG. 4. As shown, method 400 comprises conducting a step of a prepreg/laminate manufacturing process at step 404, measuring at least two properties of the prepreg/laminate at step 406, and analyzing the data obtained at step 408. The analysis of the data may then be utilized to adjust the manufacturing process, if necessary or desired, as shown at step 402.

In some embodiments, the data may be manipulated in order to predict how defects in the uncured, or "green-state", prepreg and/or laminate may present in the cured part. In the same, or other embodiments, the data may be manipulated in order to correlate any defects detected in the measuring steps to cured part strength. In other words, the data may be manipulated in more than one way, to provide more than one indication. In some embodiments, for example, the data may be manipulated to provide both a prediction of how defects in green-state parts will present in cured parts, and what impact these defects will have in the cured part strength.

Process modeling software and techniques are well known in the art, and these may also be applied to the data obtained during practice of the methods to predict, e.g., defects that may remain, or be exacerbated in a cured part from green state indications, and the impact any such defects may have on the cured part strength. For example, suitable methods for conducting such analysis are described, for example, in Sridhar Ranganathan, Suresh G. Advani, and Mark A. Lamontia, "A Non-Isothermal Process Model for Consolidation and Void Reduction during In-Situ Tow Placement of Thermoplastic Composites," Journal of Composite Materials, 1995 vol. 29, pp. 1040-1062; Yerramalli, C. S., Waas, A. M., "A nondimensional number to classify composite compressive failure," Journal of Applied Mechanics, Transactions ASME, 2004, vol. 71, no. 3, pp. 402-408 and Yerramalli, C. S., Waas, A. M., "A failure criterion for fiber reinforced polymer composites under combined compression-torsion loading", International Journal of Solids and Structures, 2003, vol. 40, no. 5, pp. 1139-1164, hereby incorporated herein by reference for any and all purposes.

Such analysis can be used, in some embodiments, to make changes to the process in order to minimize, or even eliminate, defect formation. Such embodiments thus provide the advantage of a reduction in reworking, or scrap, of defective articles made by the process. Such process modifications may either be made manually, or via an automated controller operatively disposed relative to the processor in order to receive information therefrom, and relative to the prepreg and/or layup apparatus, in order to provide information thereto.

The present methods are advantageously and readily incorporated into any apparatus for the manufacture of a prepreg and/or laminate, and so, such apparatus are also provided herein. Generally speaking, the apparatus comprises a controller, a resin infusion apparatus, at least one measurement apparatus, and a processor. The processor is operatively disposed relative to the measurement apparatus and controller so that information may be transmitted therebetween. In some embodiments, the apparatus may also comprise a layup apparatus.

The at least one measurement apparatus may be positioned at any location wherein data related to the prepreg and/or laminate can be, and is desirably, collected. In some embodiments, the same type of measurement apparatus may be used at more than one location, while in the same, or in other, embodiments, at least two measurement apparatus are utilized. The measurement apparatus will depend upon the data desirably obtained, and can be chosen based upon the same. In some embodiments, an optical metrology unit is utilized, either alone or in combination with an ultrasound measurement device.

For example, in those embodiments, wherein at least one measurement provides dimensional data, and the measurement is taken with one or more optical metrology device, the device(s) may be positioned, e.g., in close proximity to the layup head, and where it will generate 2-D images of the laminate surface topography that, in turn, can be analyzed to detect and characterize any wrinkles in the surface of the laminate, e.g., as shown in FIG. 2. In those embodiments wherein ultrasound measurements are desirably taken, the ultrasound probe(s) may be placed in close proximity to the resin infusion stage and/or the compression/compaction stage, where it will collect data that can be used to generate graphs such as that shown in FIG. 3, indicative of the porosity of the prepreg/laminate at a given depth.

The data is then processed by the processor to provide data, e.g., indicative of the effect of any defects in the green state prepreg and/or laminate on the number and severity of defects the corresponding cured part and/or the impact of any such defects on cured part strength. The processed data provided to the controller, which may then adjust parameters of the process, if desired or required, to reduce the amount, or magnitude, of defects generated in the prepreg and/or laminate by the process.

Process adjustments that may impact the presence, number or impact of defects in the green state prepreg and/or laminate include, but are not limited to, tow tension, temperatures, layup speed, roller pressure, and resin content. And, the processed data may indicate, and so the controller may adjust any of these manually or automatically. Automatic control may be advantageous in some embodiments, as it provides the opportunity for a closed-loop process.

The present methods and apparatus may be utilized in connection with the manufacture of any prepreg and/or laminate, regardless of the composition thereof. Prepregs typically comprise one or more curable resins, and one or more reinforcing materials, while laminates typically comprise multiple prepregs, layered one upon another.

Generally speaking, suitable curable resins for use in prepregs and laminates include thermoplastic polymeric compositions such as polystyrene, polyethylene terephthalate, polymethylmethacrylate, polyethylene, polypropylene, polyvinylacetate, polyamide, polyvinyl chloride, polyacrylonitrile, polyesters, polyvinyl chloride, polyethylene naphthalate, polyether ketone, polysulfone, polycarbonate, and copolymers thereof.

Prepregs and laminates may also utilize thermoset resins, suitable examples of which include, but are not limited to epoxies, polyesters, vinylesters, phenolic resins, polyurethanes, polyamides, or combinations of two or more of these. Adhesive compositions particularly well suited for use in the present invention include crosslinked thermosetting systems such as polyesters, vinyl-esters epoxies (including acid, base and addition cured epoxies), polyurethanes, silicone resins, acrylate polymers, polysiloxanes, polyorganosiloxanes, and phenolics, as well as blends or hybrids of any of these.

Structural adhesives are often used in prepregs and laminates, and may be used in the prepregs and laminates prepared by the present methods and/or apparatus. Preferred structural adhesives for use in the present composite systems include polyesters, methyl methacrylates, and the like.

Any suitable reinforcing material may be infused using the apparatus, systems and methods described. For example, relatively continuous fibers, or tows, may be arranged to form a unidirectional array of fibers, a cross-plied array of fibers, or bundled in tows that are arranged to form a unidirectional array of tows, or that are woven or cross-plied to form a two-dimensional array, or that are woven or braided to form a three-dimensional fabric. For three-dimensional fabrics, sets of unidirectional tows may, for example, be interwoven transverse to each other.

Useful fibers to be included in such reinforcing materials, such as tapes or fabrics, include without limitation, glass fibers, carbon and graphite fibers, basalt fibers, polymeric fibers, including aramid fibers, boron filaments, ceramic fibers, metal fibers, asbestos fibers, beryllium fibers, silica fibers, silicon carbide fibers, and the like. The fibers may be non-conductive or conductive, depending upon the desired application of the prepreg.

The present methods may be applied in the manufacture of any article comprising a prepreg and/or laminate and are particularly advantageous when applied to large articles due to the cost associated with the manufacture of such articles, and thus, the cost of reworking or scrapping the same. The present methods may also provide particular benefit when applied to prepregs, laminates and/or articles comprising these wherein the reinforcement material comprises carbon filaments or fibers. Carbon has a significantly higher stiffness and lower mass than many other reinforcement materials, e.g., glass composites. Thus, its use as a reinforcement material can enable the manufacture of prepregs, laminates and articles that may be larger, and yet lighter, with yet acceptable strength for the desired application. However, the final strength of components made of prepregs and/or laminates comprising carbon can depend greatly on the manufacturing process. Defects such as wrinkles, delaminations, porosity and voids can greatly reduce the final strength of the composite by introducing stress concentrators into the material structure that may cause localized premature failure or redirect stresses from applied loads in ways that are not accounted for in the design of the component.

Examples of industries wherein large scale articles are routinely manufactured from prepregs and/or laminates, and/or prepregs and/or laminates comprising a carbon containing reinforcement material include the energy industry, where large segments of, e.g., pipeline or other plant apparatus, may find benefit from application of the principles discussed herein. Examples of particular applications further include wind turbine components, such as, turbine blades or subcomponents of such, e.g. spars, spar caps, airfoil skins, or the cylindrical root section or tower sections of wind turbines. Laminates prepared from prepregs prepared using the methods and apparatus described may also be used in aviation applications, such as wing skins, fuselage skins, spars, or flat laminates such as ribs.

Those skilled in the art will appreciate that the conception, upon which the disclosure is based, may readily be utilized as a basis for designing other structures, methods, and/or systems for carrying out the several purposes of the present invention. It is important, therefore, that the claims be regarded as including such equivalent constructions insofar as they do not depart from the spirit and scope of the present invention.

While the disclosed embodiments of the subject matter described herein have been shown in the drawings and fully described above with particularity and detail in connection with several exemplary embodiments, it will be apparent to those of ordinary skill in the art that many modifications, changes, and omissions are possible without materially departing from the novel teachings, the principles and concepts set forth herein, and advantages of the subject matter recited in the appended claims. Hence, the proper scope of the disclosed innovations should be determined only by the broadest interpretation of the appended claims so as to encompass all such modifications, changes, and omissions. In addition, the order or sequence of any process or method steps may be varied or re-sequenced according to alternative embodiments.

What is claimed is:

1. An apparatus for the manufacture of a prepreg and/or laminate comprising
   A resin infusion apparatus;
   A layup apparatus;
   An optical metrology unit for measuring at least one first property of the prepeg and/or the laminate, said at least one first property including surface topography;
   An ultrasound probe for measuring at least one second property of the prepeg and/or the laminate, said at least one second property including porosity;
   A controller for making adjustments in the operation of the resin infusion apparatus and/or the layup apparatus based on the at least one first property and the at least one second property; and
   A processor operatively disposed relative to the optical metrology unit and the ultrasound probe and the controller so that information may be transmitted therebetween.

2. An article comprising a prepreg prepared using the apparatus of claim 1.

3. The article of claim 2, comprising a turbine component.

4. The article of claim 3, wherein the turbine component comprises a spar, spar cap, airfoil skin, or the cylindrical root section or tower sections of a wind turbine.

5. The article of claim 2, comprising an aviation component.

6. The article of claim 5, wherein the aviation component comprises a wing skin, fuselage skin, spar, or flat laminate.

7. A closed loop method for the manufacture of a prepreg and/or laminate comprising:
- conducting a step of a prepreg and/or laminate manufacturing process;
- measuring at least two properties of the prepreg and/or laminate, said at least two properties including surface topography and porosity;
- analyzing the measured at least two properties; and
- adjusting the manufacturing process according to the analysis of the measured at least two properties.

* * * * *

UNITED STATES PATENT AND TRADEMARK OFFICE
CERTIFICATE OF CORRECTION

PATENT NO. : 8,522,614 B2  
APPLICATION NO. : 12/787464  
DATED : September 3, 2013  
INVENTOR(S) : May et al.

Page 1 of 1

It is certified that error appears in the above-identified patent and that said Letters Patent is hereby corrected as shown below:

On the Title Page, in Item (75), under "Inventors", in Column 1, Line 1, delete "Michael" and insert -- Michal --, therefor.

On the Title Page, in Item (56), under "OTHER PUBLICATIONS", in Column 2, Line 1, delete "forthe" and insert -- for the --, therefor.

In the Specification

In Column 4, Line 16, delete " (SQUIDS)" and insert -- (SQUIDs) --, therefor.

In the Claims

In Column 8, Line 49, in Claim 1, delete "comprising" and insert -- comprising: --, therefor.

In Column 8, Line 53, in Claim 1, delete "prepeg" and insert -- prepreg --, therefor.

In Column 8, Line 56, in Claim 1, delete "prepeg" and insert -- prepreg --, therefor.

Signed and Sealed this  
Fifth Day of November, 2013

Teresa Stanek Rea  
*Deputy Director of the United States Patent and Trademark Office*